United States Patent
Uneme et al.

(10) Patent No.: US 9,725,418 B2
(45) Date of Patent: Aug. 8, 2017

(54) PYRIMIDINE COMPOUND

(71) Applicant: Sumitomo Chemical Company, Limited, Tokyo (JP)

(72) Inventors: Hideki Uneme, Takarazuka (JP); Ganesh Balkrishna Salunke, Pune (IN)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/129,220

(22) PCT Filed: Mar. 16, 2015

(86) PCT No.: PCT/JP2015/058639
§ 371 (c)(1),
(2) Date: Sep. 26, 2016

(87) PCT Pub. No.: WO2015/146870
PCT Pub. Date: Oct. 1, 2015

(65) Prior Publication Data
US 2017/0101382 A1    Apr. 13, 2017

(30) Foreign Application Priority Data

Mar. 28, 2014 (JP) ................................. 2014-067947

(51) Int. Cl.
C07D 239/42 (2006.01)
A01N 43/54 (2006.01)

(52) U.S. Cl.
CPC ........... C07D 239/42 (2013.01); A01N 43/54 (2013.01)

(58) Field of Classification Search
CPC ..... C07D 239/42; A01N 43/54; A61K 31/505
USPC .......................................... 544/326; 514/256
See application file for complete search history.

(56) References Cited

FOREIGN PATENT DOCUMENTS

| | | |
|---|---|---|
| EP | 0057440 A1 | 8/1982 |
| EP | 0264217 A2 | 4/1988 |
| EP | 0665225 A1 | 8/1995 |
| JP | S57176967 A | 10/1982 |
| JP | S63225364 A | 9/1988 |
| JP | H06502864 A | 3/1994 |
| JP | H 07258223 A | 10/1995 |
| WO | 9208704 A1 | 5/1992 |

OTHER PUBLICATIONS

Int'l Preliminary Report on Patentability issued Oct. 4, 2016 in Int'l Application No. PCT/JP2015/058639.
Int'l Search Report and Written Opinion issued Jun. 23, 2015 in Int'l Application No. PCT/JP2015/058639.

*Primary Examiner* — Deepak Rao
(74) *Attorney, Agent, or Firm* — Panitch Schwarze Belisario & Nadel LLP

(57) ABSTRACT

Provided are a pyrimidine compound represented by formula (1) having excellent harmful pest-exterminating potency, a harmful pest-exterminating agent comprising the compound and an inert carrier, and a method for exterminating harmful pests whereby the effective dose of the compound is used on harmful pests or on areas where harmful pests grow.

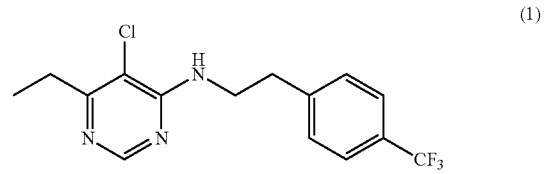

(1)

3 Claims, No Drawings

PYRIMIDINE COMPOUND

CROSS-REFERENCE TO RELATED APPLICATION

This application is a Section 371 of International Application No. PCT/JP2015/058639, filed Mar. 16, 2015, which was published in the Japanese language on Oct. 1, 2015, under International Publication No. WO 2015/146870 A1, and the disclosure of which is incorporated herein by reference.

TECHNICAL FIELD

The present invention relates to a pyrimidine compound and a use of the same for controlling pests.

BACKGROUND ART

Hitherto, a certain pyrimidine compound has been known as active ingredient for a pest control agent (for example, see Patent Literatures 1 to 3).

CITATION LIST

Patent Documents

[Patent Literature-1]: WO 1992/08704 pamphlet
[Patent Literature-2]: EP 665225 A1
[Patent Literature-3]: EP 264217 A1

SUMMARY OF INVENTION

Problems to be Solved by Invention

An object of the present invention is to provide novel compound having an efficacy for controlling pests.

Means to Solve Problems

The present inventors have intensively studied to find out a compound having an efficacy for controlling pests. As a result, they have found out that a compound represented by the below-mentioned (1) has an efficacy for controlling pests, which thus have completed the present invention.

That is, the present invention includes:
[1] A pyrimidine compound represented by formula (1):

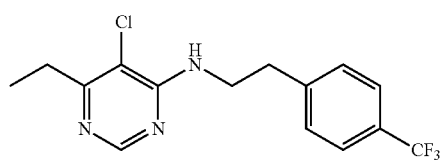 [SMILES: CCc1ncnc(NCCc2ccc(C(F)(F)F)cc2)c1Cl]

(1)

(hereinafter, referred to as a present compound).
[2] An agent for controlling pests comprising the pyrimidine compound represented by formula (1) and an inert active carrier.
[3] A method for controlling pests comprising a process of applying an effective amount of the pyrimidine compound represented by formula (1) to a pest or a habitat where the pest lives.

MODE FOR CARRYING OUT THE INVENTION

The present compound may be mixed with, for example, hydrochloric acid, sulfuric acid or phosphoric acid to become an agriculturally acceptable salt form. The agriculturally acceptable salt form is also encompassed in the compound of the present invention.

Next, a process for preparing the compound of the present invention is described.
(Process 1)

The compound of the present invention can be prepared by reacting a compound (2) with a compound (3).

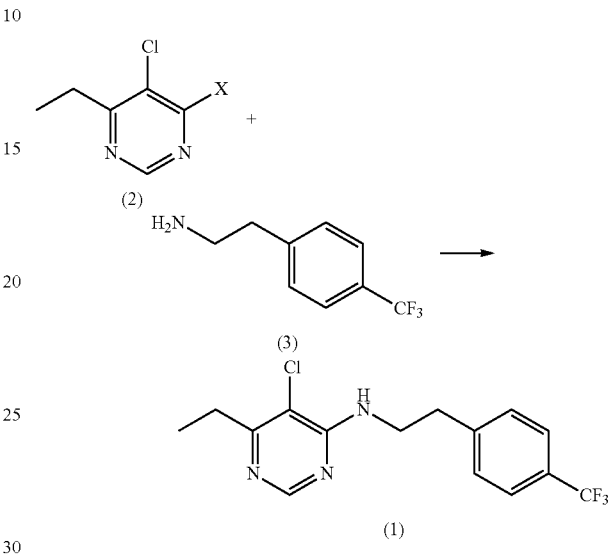

[wherein X represents a leaving group, for example, a halogen atom (such as a fluorine atom, a chlorine atom, a bromine atom, and an iodine atom), an alkylsulfonyloxy group (such as a methanesulfonyloxy group, and a trifluoromethanesulfonyloxy group), or an arylsulfonyloxy group (such as a benzenesulfonyloxy group, and a p-toluenesulfonyloxy group)]

The reaction is usually carried out in a solvent. Examples of the solvent to be used in the reaction include water; alcohols such as methanol, ethanol, and isopropyl alcohol; ketones such as acetone, and methyl ethyl ketone; ethers such as tetrahydrofuran (hereinafter, referred to as THF), diethyl ether, tert-butyl methyl ether, ethyleneglycol dimethyl ether, and 1,4-dioxane; acid amides such as N,N-dimethylformamide (hereinafter, referred to as DMF); nitriles such as acetonitrile; aromatic hydrocarbons such as toluene and xylene; aliphatic hydrocarbons such as pentane, hexane, and heptane; esters such as ethyl acetate; sulfoxides such as dimethyl sulfoxide; sulfolane; halogenated hydrocarbons such as 1,2-dichloroethane, chloroform and chlorobenzene; and mixed solvents thereof.

The compound (3) may be used as itself or a salt composed of the compound (3) and an acid. Examples of the acid include a hydrochloric acid, a sulfuric acid, and a phosphoric acid.

The used amount of the compound (3) includes usually 0.5 to 5 molar ratios(s) as opposed to one (1) mole of the compound (2).

The reaction is usually carried out in a base. Examples of the base used in the reaction include alkali metal hydrides such as sodium hydride; carbonates such as sodium carbonate, potassium carbonate, and cesium carbonate; alkali metal hydroxides such as sodium hydroxide and potassium hydroxide; alkali metal alkoxides such as potassium tert-butoxide; and organic bases such as triethylamine, pyridine, 1,8-diazabicyclo[5.4.0]undeca-7-ene. The used amount of the base includes usually 1 to 5 molar ratio(s) as opposed to 1 mole of the compound (2).

The reaction may be also carried out in the presence of a phase transfer catalyst. Examples of the phase transfer catalyst include quaternary ammonium salts such as tetrabutylammonium bromide, and benzyltriethylammonium chloride. The used amount of the phase transfer catalyst includes usually 0.01 to 0.5 molar ratios as opposed to 1 mole of the compound (2).

The reaction temperature is usually within a range of 0 to 150° C., and the reaction period is usually within a range of 0.1 to 24 hour(s).

When the reaction is completed, the reaction mixtures are extracted with organic solvent(s), and the resulting organic layers are worked up (for example, drying and concentration) to isolate the compound of the present invention. The isolated present compound may be further purified, for example, by chromatography or recrystallization.

In the above process, the compound (2) is a publically known compound, or can be prepared from a publically known compound according to a publically known method. The compound (3) is a publically known compound.

The pests on which the present compound has a control efficacy include, for example, harmful arthropods such as harmful insects and harmful mites, and nematodes. The specific examples of the pests include the followings:

Hemiptera:
 Delphacidae (for example, *Laodelphax striatella*, *Nilaparvata lugens*, or *Sogatella furcifera*),
 Deltocephalidae (for example, *Nephotettix cincticeps*, *Nephotettix virescens*, or *Empoasca onukii*),
 Aphididae (for example, *Aphis gossypii*, *Myzus persicae*, *Brevicoryne brassicae*, *Aphis spiraecola*, *Macrosiphum euphorbiae*, *Aulacorthum solani*, *Rhopalosiphum padi*, *Toxoptera citricidus*, or *Hyalopterus pruni*),
 Pentatomidae (for example, *Nezara antennata*, *Riptortus clavetus*, *Leptocorisa chinensis*, *Eysarcoris parvus*, or *Halyomorpha mista*),
 Aleyrodidae (for example, *Trialeurodes vaporariorum*, *Bemisia tabaci*, *Dialeurodes citri*, or *Aleurocanthus spiniferus*),
 Coccoidea (for example, *Aonidiella aurantii*, *Comstockaspis perniciosa*, *Unaspis citri*, *Ceroplastes rubens*, *Icerya purchasi*, *Planococcus kraunhiae*, *Pseudococcus longispinis*, *Pseudaulacaspis pentagona*),
 Tingidae,
 Cimicoidea (for example, *Cimex lectularius*),
 Psyllidae,
 and the others.

Lepidoptera:
 Pyralidae (for example, *Chilo suppressalis*, *Tryporyza incertulas*, *Cnaphalocrocis medinalis*, *Notarcha derogata*, *Plodia interpunctella*, *Ostrinia furnacalis*, *Hellula undalis*, or *Pediasia teterrellus*),
 Noctuidae (for example, *Spodoptera litura*, *Spodoptera exigua*, *Pseudaletia separata*, *Mamestra brassicae*, *Agrotis ipsilon*, *Plusia nigrisigna*, *Trichoplusia* spp., *Heliothis* spp., or *Helicoverpa* spp.),
 Pieridae (for example, *Pieris rapae*),
 *Adokisofiesu* genus,
 Tortricidae (for example, *Grapholita molesta*, *Leguminivora glycinivorella*, *Matsumuraeses azukivora*, *Adoxophyes orana fasciata*, *Adoxophyes honmai*., *Homona magnanima*, *Archips fuscocupreanus*, or *Cydia pomonella*),
 Gracillariidae (for example, *Caloptilia theivora*, or *Phyllonorycter ringoneella*),
 Carposinidae (for example, *Carposina niponensis*),
 Lyonetiidae (for example, *Lyonetia* spp.),
 Lymantriidae (for example, *Lymantria* spp., or *Euproctis* spp.),
 Yponomeutidae (for example, *Plutella xylostella*),
 Gelechiidae (for example, *Pectinophora gossypiella*, or *Phthorimaea operculella*),
 Arctiidae (for example, *Hyphantria cunea*),
 Tineidae (for example, *Tinea translucens*, or *Tineola bisselliella*),
 and the others.

Thysanoptera:
 Thysanopterae (for example, *Frankliniella occidentalis*, *Thrips palmi*, *Scirtothrips dorsalis*, *Thrips tabaci*, *Frankliniella intonsa*), and the others.

Diptera:
 House mosquitoes (*Culex* spp.) (for example, *Culex pipiens pallens*, *Culex tritaeniorhynchus*, or *Culex quinquefasciatus*),
 *Aedes* spp. (for example, *Aedes aegypti*, or *Aedes albopictus*),
 *Anopheles* spp. (for example, *Anopheles sinensis*, or *Anopheles gambiae*),
 Chironomidae,
 Muscidae (for example, *Musca domestics*, or *Muscina stabulans*),
 Calliphoridae,
 Sarcophagidae,
 Fanniidae,
 Anthomyiidae (for example, *Delia platura*, or *Delia antiqua*),
 Agromyzidae (for example, *Agromyza oryzae*, *Hydrellia griseola*, *Liriomyza sativae*, *Liriomyza trifolii*, or *Chromatomyia horticola*),
 Chloropidae (for example, *Chlorops oryzae*),
 Tephritidae (for example, *Dacus cucurbitae*, or *Ceratitis capitata*),
 Drosophilidae,
 Phoridae (for example, *Megaselia spiracularis*),
 Psychodidae (for example, *Clogmia albipunctata*),
 Sciaridae,
 Simuliidae,
 Tabanidae (for example, *Tabanus trigonus*),
 Hippoboscidae,
 Stomoxyidae,
 and the others.

Coleoptera:
 Corn root worms (*Diabrotica* spp.) (for example, *Diabrotica virgifera virgifera*, or *Diabrotica undecimpunctata howardi*),
 Scarabaeidae (for example, *Anomala cuprea*, *Anomala rufocuprea*, or *Popillia japonica*),
 Curculionidae (for example, *Sitophilus zeamais*, *Lissorhoptrus oryzophilus*, *Callosobruchuys chienensis*, *Echinocnemus squameus*, *Anthonomus grandis*, or *Sphenophorus venatus*),
 Tenebrionidae (for example, *Tenebrio molitor*, or *Tribolium castaneum*),
 Chrysomelidae (for example, *Oulema oryzae*, *Aulacophora femoralis*, *Phyllotreta striolata*, or *Leptinotarsa decemlineata*),
 Dermestidae (for example, *Anthrenus verbasci*, *Dermestes maculates*),
 Anobiidae (for example, *Lasioderma serricorne*),
 *Epilachna* (for example, *Epilachna vigintioctopunctata*),
 Scolytidae (for example, *Lyctus brunneus*, or *Tomicus piniperda*),
 Bostrichidae, Ptinidae,
Cerambycidae (for example, *Anoplophora malasiaca*),
Elateridae (*Agriotes* spp.), and
*Paederus fuscipes*,
and the others.

Orthoptera:
*Locusts migratoria, Gryllotalpa africana, Oxya yezoensis, Oxya japonica, Grylloidea*, and the others.

Siphonaptera:
*Ctenocephalides felis, Ctenocephalides canis, Pulex irritans, Xenopsylla cheopis*, and the others.

Anoplura:
*Pediculus humanus corporis, Pediculus humanus humanus, Phthirus pubis, Haematopinus eurysternus, Linognathus ovillus, Haematopinus suis, Linognathus setosus* and the others.

Mallophaga:
*Bovicola ovis, Dalmalinia Bovis, Menopon gallinae, Trichodectes canis, Felicola subrostrata*, and the others.

Hymenoptera:
Formicidae (for example, *Monomorium pharaosis, Formica fusca japonica, Ochetellus glaber, Pristomyrmex pungens, Pheidole noda, Acromyrmex* spp., *Solenopsis* spp., *Linepithema humile*),
Vespidae,
Betylidae,
Tenthredinidae (for example, *Athalia rosae*, or *Athalia japonica*),
and the others.

Nematodes:
*Aphelenchoides besseyi, Nothotylenchus acris, Meloidogyne incognita, Meloidogyne hepla, Meloidogyne javanica, Heterodera glycines, Globodera rostochiensis, Pratylenchus coffeae, Pratylenchus neglectus*, and the others.

Blattariae:
*Blattella germanica, Periplaneta fuliginosa, Periplaneta americana, Periplaneta brunnea, Blatta orientalis*, and the others.

Isoptera:
*Reticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Glyptotermes kodamai, Glyptotermes kushimensis, Hodotermopsis japonica, Coptotermes guangzhoensis, Reticulitermes miyatakei, Reticulitermes flaviceps amamianus, Reticulitermes* sp., *Nasutitermes takasagoensis, Pericapritermes nitobei, Sinocapritermes mushae*, and the others.

Acarina:
Tetranychidae (for example, *Tetranychus urticae, Tetranychus kanzawai, Panonychus citri, Panonychus ulmi*, or *Oligonychus* spp.),
Eriophyidae (for example, *Aculops pelekassi, Phyllocoptruta citri, Aculops lycopersici, Calacarus carinatus, Acaphylla theavagrans, Eriophyes chibaensis*, or *Aculus schlechtendali*),
Tarsonemidae (for example, *Polyphagotarsonemus latus*),
Tenuipalpidae (for Example, *Brevipalpus phoenicis*),
Tuckerellidae,
Ixodidae (for example, *Haemaphysalis longicornis, Haemaphysalis flava, Dermacentor taiwanicus, Dermacentor variabilis, Ixodes ovatus, Ixodes persulcatus, Ixodes scapularis, Amblyomma americanus, Boophilus microplus*, or *Rhipicephalus sanguineus*),
Acaridae (for example, *Tyrophagus putrescentiae*, or *Tyrophagus similis*),
Pyroglyphidae (for example, *Dermatophagoides farinae*, or *Dermatophagoides ptrenyssnus*),
Cheyletidae (for example, *Cheyletus eruditus, Cheyletus malaccensis, Cheyletus moorei*, or *Cheyletiella yasguri*),
Sarcoptidae (for example, *Octodectes cynotis*, or *Sacroptes scabiei*),
*Demodex folliculorum* (for example, *Demodex canis*),
Listrophoridae,
Oribatid mites,
Dermanyssidae (for example, *Ornithonyssus bacoti, Ornithonyssus sylvairum*, or *Dermanyssus gallinae*),
trombiculid mites (for example, *Leptotrombidium akamushi*),
and the others.

Araneae:
*Chiracanthium japonicum*, or *Latrodectus hasseltii*, and the others.

Chilopoda:
*Thereuonema hilgendorfi*, or *Scolopendra subspinipes*, and the others.

Diplopoda:
*Oxidus gracilis*, or *Nedyopus tambanus*, and the others.

Isopoda:
*Armadillidium vulgare*, and the others.

Gastropoda:
*Limax marginatus*, or *Limax flavus*, and the others.

The agent for controlling pest of the present invention comprises the present compound and an inert active carrier. The active inert carrier used herein represents an extender, a diluent and the others that are used in a disease prevention field and an agricultural field. The agent for controlling pests of the present invention is usually prepared by mixing the present compound with an inert active carrier such as solid carrier, liquid carrier or gaseous carrier, and if necessary, adding surfactants and the other auxiliary agents for formulation, to formulate into emulsifiable concentrates, oil solutions, dust formulations, granules, wettable powders, flowables, microcapsules, aerosols, smoking agents, poison baits, resin formulations, shampoo formulations, paste-like formulations, foams, carbon dioxide formulations and tablets and the others. Such formulations may be processed into mosquito repellent coils, electric mosquito repellent mats, liquid mosquito formulations, smoking agents, fumigants, sheet formulations, spot-on formulations or formulations for oral treatment.

The agent for controlling pests of the present invention comprises usually 0.01 to 95% by weight of the present compound.

Examples of the solid carrier to be used in the formulation include fine powders or granules of clays (for example, kaolin clay, diatomaceous earth, bentonite, Fubasami clay, or acid white clay), synthetic hydrated silicon oxides, talcs, ceramics, other inorganic minerals (for example, sericite, quartz, sulfur, active carbon, calcium carbonate or hydrated silica) or chemical fertilizers (for example, ammonium sulfate, ammonium phosphate, ammonium nitrate, urea or ammonium chloride) and the others; as well as synthetic resins (for example, polyester resins such as polypropylene, polyacrylonitrile, polymethylmethacrylate and polyethylene terephthalate; nylon resins (for example, nylon-6, nylon-11 and nylon-66); polyamide resins; polyvinyl chloride, polyvinylidene chloride, vinyl chloride-propylene copolymers, and the others.

Examples of the above-mentioned liquid carriers include water; alcohols (for example, methanol, ethanol, isopropyl alcohol, butanol, hexanol, benzyl alcohol, ethylene glycol, propylene glycol or phenoxy ethanol); ketones (for example, acetone, methyl ethyl ketone or cyclohexanone); aromatic hydrocarbons (for example, toluene, xylene, ethyl benzene, dodecyl benzene, phenyl xylyl ethane or methylnaphthalene); aliphatic hydrocarbons (for example, hexane, cyclohexane, kerosene or light oil); esters (for example, ethyl acetate, butyl acetate, isopropyl myristate, ethyl oleate, diisopropyl adipate, diisobutyl adipate or propylene glycol monomethyl ether acetate); nitriles (for example, acetonitrile or isobutyronitrile); ethers (for example, diisopropyl ether, 1,4-dioxane, ethyleneglycol dimethyl ether, diethyleneglycol dimethyl ether, diethylene glycol monomethyl ether, propylene glycol monomethyl ether, dipropylene glycol monomethyl ether or 3-methoxy-3-methyl-1-butanol); acid amides (for example, N,N-dimethylformamide or N,N-dimethylacetamide); halogenated hydrocarbons (for example, dichloromethane, trichloroethane or carbon tetrachloride); sulfoxides (for example, dimethyl sulfoxide); propylene carbonate; and vegetable oils (for example, soybean oil or cottonseed oil).

Examples of the above-mentioned gaseous carrier include fluorocarbon, butane gas, liquefied petroleum gas (LPG), dimethyl ether, and carbon dioxide gas.

Examples of the surfactants include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer. Specific examples thereof include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol).

Examples of base material of the resin formulation include polyvinyl chloride polymers, polyurethane and the others, and a plasticizer such as phthalate esters (for example, dimethyl phthalate, dioctyl phthalate), adipic acid esters and stearic acid may be added to these base materials, if necessary. The resin formulation can be prepared by kneading the compound of the present invention into the above-mentioned base material with a usual kneading apparatus, followed by molding the resultant mixture by injection molding, extrusion molding or pressure molding and the like. The resultant resin formulation can be subjected to further molding or cutting procedure and the like, if necessary, to be processed into shapes such as a plate, film, tape, net or string shape. These resin formulations can be processed into animal collars, animal ear tags, sheet products, trap strings, gardening supports and other products.

Examples of a base material for the poison baits include bait ingredients such as grain powder, vegetable oil, saccharide and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, insect attraction fragrances such as cheese flavor, onion flavor and peanut oil.

The agent for controlling pests of the present invention may be applied to a pest directly and/or or a habitat thereof to control a pest.

The method for controlling pests of the present invention is conducted by applying an effective amount of the compound of the present invention to a pest directly and/or a habitat thereof (for example, plant bodies, soil, inside a house, animal bodies). In the method for controlling pests of the present invention, the compound of the present invention is usually used in the form of a pest control agent.

When the agent for controlling pests of the present invention is used for controlling pests in an agricultural field, the application dose as an amount of the compound of the present invention is usually within a range from 1 to 10,000 g per 10,000 $m^2$. When the agent for controlling pests is formulated into the emulsifiable concentrate, the wettable powder, or the flowable formulation etc., these formulations are usually applied by diluting them with water in such a way that a concentration of the active ingredient is within a range from 0.01 to 10,000 ppm. The granular formulation, or the dust formulation etc., is usually applied as itself without diluting it.

These formulations or a water dilution solution thereof can be sprayed directly to pests or plants to be protected from pests, and also may be applied to the soil of crop land in order to control pests which live there.

Also, the resin preparation which is processed into a sheet or a string may be applied by winding a crop with a sheet or a string of the resin preparation, putting a string of the resin preparation around a crop so that the crop is surrounded by the string, or laying a sheet of the resin preparation on the soil surface near the root of a crop.

When the agent for controlling pests of the present invention is used to control pests that live inside a house, the application dose as an amount of the compound of the present invention is usually within a range from 0.01 to 1,000 mg per 1 $m^2$ of an area to be treated, in the case of using it on a planar area. In the case of using it spatially, the application dose as an amount of the compound of the present invention is usually within a range from 0.01 to 500 mg per 1 $m^3$ of the space to be treated. When the pest control agent of the present invention is formulated into emulsifiable concentrates, wettable powders or the others, such formulations are usually applied after diluting them with water in such a way that a concentration of the active ingredient is within a range from 0.1 to 10,000 ppm, and then sparging it. In the case of being formulated into oil solutions, aerosols, smoking agents, poison baits and the others, such formulations are used as itself without diluting it.

When the agent for controlling pests of the present invention is sued for controlling external parasites of livestock such as cows, horses, pigs, sheep, goats and chickens and small animals such as dogs, cats, rats and mice, the agent for controlling pests of the present invention can be applied to the livestock or the animals by a known method in the veterinary field. Specifically, when systemic control is intended, the pest control agent of the present invention is administered to the animals as a tablet, a mixture with feed or a suppository, or by injection (including intramuscular, subcutaneous, intravenous and intraperitoneal injections). On the other hand, when non-systemic control is intended, the pest control agent of the present invention is applied to the animals by means of spraying of the oil solution or aqueous solution, pour-on or spot-on treatment, or washing of the animal with a shampoo formulation, or by putting a collar or ear tag made of the resin formulations to the animal. In the case of administering to an animal body, the dose of the compound of the present invention is usually within a range from 0.1 to 1,000 mg per 1 kg of an animal body weight.

The agent for controlling pests of the present invention can be used in an agricultural land where plant as below-mentioned is cultivated.

Crops:

corn, rice, wheat, barley, rye, oat, sorghum, cotton, soybean, peanut, buckwheat, beet, rapeseed, sunflower, sugar cane, tobacco, and the others;

Vegetables:

solanaceous vegetables (for example, eggplant, tomato, pimento, pepper or potato), cucurbitaceous vegetables (for example, cucumber, pumpkin, zucchini, water melon or melon), cruciferous vegetables (for example, Japanese radish, white turnip, horseradish, kohlrabi, Chinese cabbage, cabbage, leaf mustard, broccoli, cauliflower), asteraceous vegetables (for example, burdock, crown daisy, artichoke or lettuce), liliaceous vegetables (for example, green onion, onion, garlic or asparagus), ammiaceous vegetables (for example, carrot, parsley, celery or parsnip), chenopodiaceous vegetables (for example, spinach or Swiss chard), lamiaceous vegetables (for example, *Perrila frutescens*, mint or basil), strawberry, sweet potato, *Dioscorea japonica*, colocasia or the others;

Fruits:

pomaceous fruits (for example, apple, pear, Japanese pear, Chinese quince or quince), stone fleshy fruits (for example, peach, plum, nectarine, *Prunus mume*, cherry fruit, apricot or prune), citrus fruits (for example, *Citrus unshiu*, orange, lemon, lime or grapefruit), nuts (for example, chestnut, walnuts, hazelnuts, almond, pistachio, cashew nuts or macadamia nuts), berry fruits (for example, blueberry, cranberry, blackberry or raspberry), grape, kaki persimmon, olive, Japanese plum, banana, coffee, date palm, coconuts, oil palm and the others;

Trees Other than Fruit Trees:

tea, mulberry, flowering plant (for example, dwarf azalea, camellia, hydrangea, sasanqua, *Illicium anisatum*, cherry trees, tulip tree, crape myrtle or fragrant olive), roadside trees (for example, ash, birch, dogwood, *Eucalyptus, Ginkgo biloba*, lilac, maple, *Quercus*, poplar, Judas tree, *Liquidambar formosana*, plane tree, zelkova, Japanese arborvitae, fir wood, hemlock, juniper, *Pinus, Picea, Taxus cuspidate*, elm or Japanese horse chestnut), Sweet viburnum, *Podocarpus macrophyllus*, Japanese cedar, Japanese cypress, croton, Japanese spindletree and *Photinia glabra*;

Lawn:

sods (for example, *Zoysia japonica, Zoysia matrella*), bermudagrasses (for example, *Cynodon dactylon*), bent glasses (for example, *Agrostis gigantea, Agrostis stolonifera, Agrostis capillaris*), blueglasses (for example, *Poa pratensis, Poa trivialis*), festucae (for example, *Festuca arundinacea* Schreb., *Festuca rubra* L. var. *commutata* Gaud., *Festuca rubra* L. var. *genuina* Hack), ryegrassses (for example, *Lolium multiflorum* Lam, *Lolium perenne* L),

*Dactylis glomerata, Phleum pretense;*

Others:

flowers (for example, rose, carnation, chrysanthemum, Eustoma, gypsophila, gerbera, marigold, salvia, petunia, verbena, tulip, aster, gentian, lily, pansy, cyclamen, orchid, lily of the valley, lavender, stock, ornamental cabbage, primula, poinsettia, gladiolus, cattleya, daisy, cymbidium or begonia), bio-fuel plants (for example, Jatropha, safflower, camelina, switchgrass, Miscanthus, reed canary grass, giant reed, Kenaf, cassava, willow, algae), ornamental foliage plants, and the others.

The above-mentioned plants include genetically modified plants thereof.

The agent for controlling pests of the present invention can be mixed or combined with other pesticides, miticides, nematicides, fungicides, plant growth regulators, herbicides, synergists and phytotoxicity reducing agents. Examples of each active ingredient for the above-mentioned pesticides, miticides, nematicides, fungicides, herbicides, synergists and phytotoxicity reducing agents respectively include the followings.

Active Ingredient for Pesticides (1) Organophosphorous Compound acephate, Aluminum Phosphide, butathiofos, cadusafos, chlorethoxyfos, chlorfenvinphos, chlorpyrifos, chlorpyrifos-methyl, cyanophos (abbrev. CYAP), diazinon, DCIP (dichlorodiisopropyl ether), dichlofenthion (abbrev. ECP), dichlorvos (abbrev. DDVP), dimethoate, dimethylvinphos, disulfoton, EPN, ethion, ethoprophos, etrimfos, fenthion (abbrev. MPP), fenitrothion (abbrev. MEP), fosthiazate, formothion, Hydrogen phosphide, isofenphos, isoxathion, malathion, mesulfenfos, methidathion (abbrev. DMTP), monocrotophos, naled (abbrev. BRP), oxydeprofos (abbrev. ESP), parathion, phosalone, phosmet (abbrev. PMP), pirimiphos-methyl, pyridafenthion, quinalphos, phenthoate (abbrev. PAP), profenofos, propaphos, prothiofos, pyraclorfos, salithion, sulprofos, tebupirimfos, temephos, tetrachlorvinphos, terbufos, thiometon, trichlorphon (abbrev. DEP), vamidothion, phorate, cadusafos, and the others.

(2) Carbamate Compounds alanycarb, bendiocarb, benfuracarb, carbaryl, carbofuran, carbosulfan, cloethocarb, ethiofencarb, fenobucarb, fenothiocarb, fenoxycarb, furathiocarb, isoprocarb (abbrev. MIPC), metolcarb, methomyl, methiocarb, oxamyl, pirimicarb, propoxur (abbrev. PHC), XMC, thiodicarb, xylylcarb, aldicarb, and the others.

(3) Pyrethroid Compounds acrinathrin, allethrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, profluthrin, dimefluthrin, 2,3,5,6-tetrafluoro-4-(methoxymethyl)benzyl (EZ)-(1RS, 3RS; 1RS, 3SR)-2,2-dimethyl-3-prop-1-enyl cyclopropanecarboxylate, 2,3,5,6-tetrafluoro-4-methylbenzyl (EZ)-(1RS, 3RS; 1RS, 3SR)-2,2-dimethyl-3-prop-1-enyl cyclopropanecarboxylate, 2,3,5,6-tetrafluoro-4-(methoxymethyl)benzyl (1RS, 3RS; 1RS, 3SR)-2,2-dimethyl-3-(2-methyl-1-propenyl)cyclopropanecarboxylate, and 2,3,5,6-tetrafluoro-4-(methoxymethyl)benzyl (EZ)-(1RS, 3RS; 1RS, 3SR)-2,2-dimethyl-3-(2-cyano-1-propenyl)cyclopropanecarboxylate, and the others.

(4) Nereistoxin Compounds cartap, bensultap, thiocyclam, monosultap, bisultap, and the others.

(5) Neonicotinoid Compounds imidacloprid, nitenpyram, acetamiprid, thiamethoxam, thiacloprid, dinotefuran, clothianidin, and the others.

(6) Benzoylurea Compounds chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, triazuron, and the others.

(7) Phenylpyrazole Compounds acetoprole, ethiprole, fipronil, vaniliprole, pyriprole, pyrafluprole, and the others.

(8) Bt Toxins live spores and crystal toxins originated from *Bacillus thuringiensis*, and a mixture thereof.

(9) Hydrazine Compounds chromafenozide, halofenozide, methoxyfenozide, tebufenozide, and the others.

(10) Organochlorine Compounds aldrin, dieldrin, dienochlor, endosulfan, methoxychlor, and the others.

(11) Other Pesticide Active Ingredients machine oil, nicotine-sulfate; avermectin-B, bromopropylate, buprofezin, chlorphenapyr, cyantraniliprole, cyromazine, D-D (1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, protrifenbute, spiromesifen, sulfoxaflor, sulfur, metaflumizone, spirotetramat, pyrifluquinazone, spinetoram, chlorantraniliprole, tralopyril, diafenthiuron, a compound represented by the below-mentioned formula (K):

(K)

wherein $R^{100}$ represents a chlorine atom, a bromine atom or a trifluoromethyl group, $R^{200}$ represents a chlorine atom, a bromine atom or a methyl group, and $R^{300}$ represents a chlorine atom, a bromine atom or a cyano group, a compound represented by the below-mentioned formula (L):

(L)

wherein $R^{1000}$ represents a chlorine atom, a bromine atom or an iodine atom, and the others.

Active Ingredient for Miticides acequinocyl, amitraz, benzoximate, bifenazate, bromopropylate, chinomethionat, chlorobenzilate, CPCBS (chlorfenson), clofentezine, cyflumetofen, kelthane (which is also referred to as dicofol), etoxazole, fenbutatin oxide, fenothiocarb, fenpyroximate, fluacrypyrim, fluproxyfen, hexythiazox, propargite (abbrev. BPPS), polynactins, pyridaben, pyrimidifen, tebufenpyrad, tetradifon, spirodiclofen, spiromesifen, spirotetramat, amidoflumet, cyenopyrafen, and the others.

Active Ingredient for Nematicides

DCIP, fosthiazate, levamisol, methyisothiocyanate, morantel tartarate, imicyafos, and the others.

Active Ingredient for Fungicides azole fungicide compounds such as propiconazole, prothioconazole, triadimenol, prochloraz, penconazole, tebuconazole, flusilazole, diniconazole, bromuconazole, epoxiconazole, difenoconazole, cyproconazole, metconazole, trifiumizole, tetraconazole, myclobutanil, fenbuconazole, hexaconazole, fluquinconazole, triticonazole, bitertanol, imazalil, flutriafol and the others;

cyclic amine fungicide compounds such as fenpropimorph, tridemorph, fenpropidin and the others:

benzimidazole fungicide compounds such as carbendazim, benomyl, thiabendazole, thiophanate-methyl and the others;

procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlofluanid; folpet; kresoxim-methyl; azoxystrobin; trifloxystrobin; fluoxastrobin; picoxystrobin; pyraclostrobin; dimoxystrobin; pyribencarb; spiroxamine; quinoxyfen; fenhexamid; famoxadone; fenamidone; zoxamide; ethaboxam; amisulbrom; iprovalicarb; benthiavalicarb; cyazofamid; mandipropamid; boscalid; penthiopyrad; metrafenone; fluopiran; bixafen; cyflufenamid; proquinazid; isotianil; tiadinil, and the others.

Active Ingredient for Plant Growth Regulators ethephon, chlormequat-chloride, mepiquat-chloride, Gibberellin A (as is typified by Gibberellin A3), abscisic acid, kinetin, benzyladenine, 1,3-diphenylurea, forchlorfenuron, thidiazuron, 4-oxo-4-(2-phenylethyl)amino butyric acid, methyl 5-(trifluoromethyl)benzo[b]thiophen-2-carboxylate, 5-(trifluoromethyl)benzo[b]thiophen-2-carboxylic acid, and the others.

Active Ingredient for Herbicides (1) Phenoxy Aliphatic Acid Herbicides 2,4-PA, MCP, MCPB, phenothiol, mecoprop, fluroxypyr, triclopyr, clomeprop, naproanilide, and the others.

(2) Benzoic Acid Herbicides
2,3,6-TBA, dicamba, clopyralid, picloram, aminopyralid, quinclorac, quinmerac, and the others.
(3) Urea Herbicides
diuron, linuron, chlortoluron, isoproturon, fluometuron, isouron, tebuthiuron, methabenzthiazuron, cumyluron, daimuron, methyl daimuron, and the others.
(4) Triazine Herbicides
atrazine, ametoryn, cyanazine, simazine, propazine, simetryn, dimethametryn, prometryn, metribuzin, triaziflam, indaziflam, and the others.
(5) Bipyridinium Herbicides
paraquat, diquat and the others.
(6) Hydroxybenznitrile Herbicides
bromoxynil, ioxynil and the others.
(7) Dinitroaniline Herbicides
pendimethalin, prodiamine, trifluralin and the others.
(8) Organophosphorous Herbicides
amiprofos-methyl, bensulide, piperophos, anilofos, glyphosate, glufosinate, glufosinate-P, bialaphos, and the others.
(9) Carbamate Herbicides
di-allate, tri-allate, EPTC, butylate, benthiocarb, esprocarb, molinate, dimepiperate, swep, chlorpropham, phenmedipham, phenisopham, pyributicarb, asulam, and the others.
(10) Acid Amide Herbicides
propanil, propyzamide, bromobutide, etobenzanid, and the others.
(11) Chloroacetanilide Herbicides
acetochlor, alachlor, butachlor, dimethenamid, propachlor, metazachlor, metolachlor, pretilachlor, thenylchlor, pethoxamid, and the others.
(12) Diphenyl Ether Herbicides
acifluorfen-sodium, bifenox, oxyfluorfen, lactofen, fomesafen, chlomethoxynil, aclonifen, and the others.
(13) Cyclic Imide Herbicide
oxadiazon, cinidon-ethyl, carfentrazone-ethyl, surfentrazone, flumiclorac-pentyl, flumioxazin, pyraflufen-ethyl, oxadiargyl, pentoxazone, fluthiacet-methyl, butafenacil, benzfendizone, bencarbazone, saflufenacil, and the others.
(14) Pyrazole Herbicides
benzofenap, pyrazolate, pyrazoxyfen, topramezone, pyrasulfotole, and the others.
(15) Triketone Herbicides
isoxaflutole, benzobicyclon, sulcotrione, mesotrione, tembotrione, tefuryltrione, and the others.
(16) Aryloxyphenoxypropionic Acid Herbicides
clodinafop-propargyl, cyhalofop-butyl, diclofop-methyl, fenoxaprop-ethyl, fluazifop-butyl, haloxyfop-methyl, quizalofop-ethyl, and the others.
(17) Trione Oxyme Herbicides
alloxydim-sodium, sethoxydim, butroxydim, clethodim, cloproxydim, cycloxydim, tepraloxydim, tralkoxydim, profoxydim, and the others.
(18) Sulfonylurea Herbicides
chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfurcn, iodosulfuron-methyl-sodium, foramsulfuron, mesosulfuron-methyl, trifloxysulfuron, tritosulfuron, orthosulfamuron, flucetosulfuron, propyrisulfuron, and the others.

(19) Imidazolinone Herbicides
imazamethabenz-methyl, imazamethapyr, imazamox, imazapyr, imazaquin, imazethapyr, and the others.
(20) Sulfonamide Herbicides
flumetsulam, metosulam, diclosulam, florasulam, cloransulam-methyl, penoxsulam, pyroxsulam, and the others.
(21) Pyrimidinyloxy Benzoic Acid Herbicides
pyrithiobac-sodium, bispyribac-sodium, pyriminobac-methyl, pyribenzoxim, pyriftalid, pyrimisulfan, and the others; and
(22) Other Systematic Herbicides
bentazon, bromacil, terbacil, chlorthiamid, isoxaben, dinoseb, amitrole, cinmethylin, tridiphane, dalapon, diflufenzopyr-sodium, dithiopyr, thiazopyr, flucarbazone-sodium, propoxycarbazone-sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, methiozolin, and the others.
Active Ingredient for Synergists
piperonyl butoxide, sesamex, sulfoxide, N-(2-ethylhexyl)-8,9,10-trinorborn-5-ene-2,3-dicarboximide (MGK 264), N-declyimidazole, WARF-antiresistant, TBPT, TPP, IBP, PSCP, methyl iodide ($CH_3I$), t-phenylbutenone, diethylmaleate, DMC, FDMC, ETP, ETN, and the others.
Active Ingredients for Phytotoxicity Reducing Agents
benoxacor, cloquintocet-mexyl, cyometrinil, dichlormid, fenchlorazole-ethyl, fenclorim, flurazole, furilazole, mefenpyr-diethyl, MG191, oxabetrinil, allidochlor, isoxadifen-ethyl, cyprosulfamide, fluxofenim, 1,8-naphthalic anhydride, AD-67, and the others.

EXAMPLES

The present invention is described in more detail below by Preparation Examples, Formulation Examples and Test Examples, but the present invention should not be limited thereto.

First, Preparation Examples of the compound of the present invention are described below.

Preparation Example 1

To a mixture of 2-(4-trifluoromethylphenyl)ethylamine 2.00 g (10.57 mmol) and DMF 20 mL were added potassium carbonate 2.92 g (21.13 mmol) and 4,5-dichloro-6-ethylpyrimidine 2.06 g (11.63 mmol), and the mixture was stirred at 90° C. for 5 hours. After the mixture was cooled to a room temperature, thereto was added water 60 mL, and the mixture was extracted three times with ethyl acetate. The organic layer was washed with water and saturated saline, and then dried over anhydrous sodium sulfate, and concentrated. The resulting residue was subjected to a silica gel column chromatography to obtain 5-chloro-4-ethyl-6-[2-(4-trifluoromethylphenyl)ethyl]pyrimidine (the compound of the present invention) 3.00 g.

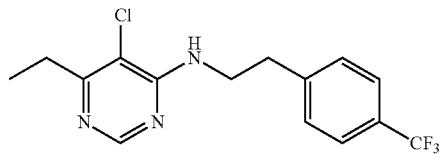

¹H-NMR (CDCl₃) δ: 1.27 (3H, t, J=7.5 Hz), 2.79 (2H, q, J=7.5 Hz), 3.00 (2H, t, J=7.0 Hz), 3.79 (2H, q, J=7.0 Hz), 5.42 (1H, bs), 7.35 (2H, d, J=7.9 Hz), 7.58 (2H, d, J=7.9 Hz), 8.45 (1H, s).

Preparation Example 2

To a mixture of triethylamine 24.2 mL (175 mmol) and toluene 140 mL were added 2-(4-trifluoromethylphenyl)ethylamine 31.8 g (purity 92%, 155 mmol) and 4,5-dichloro-6-ethylpyrimidine 20.0 g (purity 91%, 103 mmol). The mixture was stirred at 110° C. for six hours, and then cooled to a room temperature. Thereto was added water 200 mL, and the mixture was extracted twice with ethyl acetate. The organic layer was washed with saturated saline, and dried over anhydrous sodium sulfate, and concentrated. The resulting residue was recrystallized from 10% ethyl acetate/hexane to obtain 5-chloro-4-ethyl-6-[2-(4-trifluoromethylphenyl)ethyl]pyrimidine (the compound of the present invention) 22.4 g.

Next, Formulation Examples are described below. Herein, "parts" means "parts by weight".

Formulation Example 1

Nine (9) parts of the compound of the present inventions is dissolved into 37.5 parts of xylene and 37.5 parts of dimethylformamide. Thereto 10 parts of polyoxyethylene styryl phenyl ether and 6 parts of calcium dodecylbenzene sulfonate are added and mixed by stirring thoroughly to obtain an emulsifiable concentrate.

Formulation Example 2

Five (5) parts of SORPOL 5060 (registered trade name for TOHO Chemical Industry Co., LTD.) is added to 40 parts of the compound of the present invention, and mixed thoroughly. Then, 32 parts of CARPLEX #80 (registered trade name for Shionogi & Co., Ltd., synthetic hydrous silicon oxide fine powder) and 23 parts of 300 mesh diatomaceous earth are added thereto, and mixed with a juice mixer to obtain a wettable powder.

Formulation Example 3

Three (3) parts of the compound of the present invention, 5 parts of synthetic hydrous silicon oxide fine powder, 5 parts of sodium dodecylbenzenesulfonate, 30 parts of bentonite and 57 parts of clay are added, and mixed by stirring thoroughly. To this mixture an appropriate amount of water is added. The mixture is further stirred, granulated with a granulator, and then air-dried to obtain a granule.

Formulation Example 4

Four point five (4.5) parts of the compound of the present invention, 1 part of synthetic hydrous silicon oxide fine powder, 1 part of Dorires B (manufactured by Sankyo) as a flocculant, and 7 parts of clay are mixed thoroughly with a mortar, and then by stirring with a juice mixer. To the resultant mixture 86.5 parts of cut clay is added, and mixed by stirring thoroughly to obtain a dust.

Formulation Example 5

Ten (10) parts of the compound of the present invention, 35 parts of a mixture of polyoxyethylene alkylether sulfate ammonium salt and white carbon (weight ratio 1:1), 55 parts of water are mixed, and then finely-divided by a wet grinding method to obtain a formulation.

Formulation Example 6

Zero point five (0.5) part of the compound of the present invention is dissolved in 10 parts of dichloromethane. This solution is mixed with 89.5 parts of Isopar M (isoparaffin: registered trade name for Exxon Chemical) to obtain an oil solution.

Formulation Example 7

Zero point one (0.1) part of the compound of the present invention and 49.9 parts of NEO-THIOZOL (Chuo Kasei Co., Ltd.) are placed in an aerosol can. An aerosol valve is fitted to the can, and the can is then charged with 25 parts of dimethyl ether and 25 parts of LPG. The aerosol can is shaken, and an actuator is fitted to the can to obtain an oily aerosol.

Formulation Example 8

An aerosol container is charged with a mixed solution of 0.6 parts of the compound of the present invention, 0.01 parts of BHT, 5 parts of xylene, 3.39 parts of a deodorized kerosine and 1 part of an emulsifying agent [Atmos 300 (registered trade name for Atmos Chemical Ltd.)] and 50 parts of distilled water. A valve part is attached to the container, and the container is then charged with 40 parts of a propellant (LPG) through the valve under increased pressure to obtain an aqueous aerosol.

Further, an effectiveness of the compound of the present invention as an active ingredient for a pest control agent is shown by Test Examples.

Test Example 1

A formulation of the compound of the present invention that was prepared according to Formulation Example 5 was diluted with water so that the active ingredient concentration was set to 500 ppm to prepare a testing agent solution.

Twenty (20) mL of the above-mentioned testing medicinal solution was sprayed onto a cabbage (*Brassicae oleracea*) in the third to fourth leaf stage. After the testing medicinal solution was dried, the aerial part of the plant was cut, and then was installed in a polyethylene cup (volume 100 mL) together with five heads of cabbage moth (*Plutella xylostella*) at the second instar larval stages. The cup was held at 25° C. and after 5 days, the number of surviving insects was counted and the mortality was calculated according to the following equation.

Mortality (%)=(Number of dead larvae/Number of tested larvae)×100

As a result, the treatment with the compound of the present invention showed a mortality of 80% or more.

Test Example 2

A formulation of the compound of the present invention that was prepared according to Formulation Example 5 was diluted with water so that the active ingredient concentration was set to 500 ppm to prepare a testing agent solution.

The bottom of the polyethylene cup having 5.5 cm diameter was matted with the same size of a filter paper. Insecta LF (manufactured by NOSAN CORPORATION), an artificial diet, was sliced to 6 mm in thickness, cut into half, and then placed on the filter paper. Then, 2 mL of the test solution was poured into the polyethylene cup. After the test solution was air-dried, 5 fourth instar larvae of tobacco cutworm (*Spodoptera litura*) were released into the polyethylene cup and the cup was sealed with a lid. After 6 days, the number of surviving tobacco cutworm (*Spodoptera litura*) was counted and the mortality was calculated according to the following equation.

Mortality (%)=(Number of dead larvae/Number of tested larvae)×100

As a result, the treatment with the compound of the present invention showed a mortality of 80% or more.

Test Example 3

A formulation of the compound of the present invention that was prepared according to Formulation Example 5 was diluted with water so that the active ingredient concentration was set to 500 ppm to prepare a testing agent solution.

A filter paper having a diameter of 5.5 cm was spread on the bottom of a polyethylene cup having a diameter of 5.5 cm. SilkMate 2S (manufactured by NOSAN CORPORATION), an artificial diet, was sliced to 2 mm in thickness and then placed on the filter paper. Then, 1 mL of the test solution (500 ppm) was poured into the polyethylene cup. After the test solution was air-dried, the filter paper having a diameter of 5.5 cm was put on the artificial diet, and 30 first instar larvae of summer fruit tortrix (*Adoxophyes orana*) were released on the filter paper, and the cup was sealed with a lid. After 7 days, the number of surviving summer fruit tortrix was counted and mortality was calculated according to the following equation.

Mortality (%)=(Number of dead larvae/Number of tested larvae)×100

As a result, the treatment with the compound of the present invention showed a mortality of 90% or more.

Test Example 4

A formulation of the compound of the present invention that was prepared according to Formulation Example 5 was diluted with water so that the active ingredient concentration was set to 500 ppm to prepare a testing agent solution.

Rice seedling (on the developmental stage of the second true leaf) was planted in a polyethylene cup, and the above-mentioned test solutions 10 mL were sprayed. After the test solution was air-dried, twenty (20) heads of three to four instar larvae of rice planthopper (*Nilaparvata lugens*) were released and the plants were held in a greenhouse at 25° C. After 6 days, the number of the surviving insects that were parasitic on the leaves of the rice was examined and the controlling value was calculated by the following equation.

Controlling value (%)={1−($Cb$×$Tai$)/($Cai$×$Tb$)}×100 wherein the symbols in the formula represent the following descriptions.

Cb: Number of the insects before treatment in untreated area;

Cai: Number of the surviving parasitic insects at the time of the investigation in untreated area;

Tb: Number of the insects before treatment in treated area;

Tai: Number of the surviving parasitic insects at the time of the investigation in treated area;

As a result, the treatment with the compound of the present invention showed a controlling value of 90% or more.

Test Example 5

A formulation of the compound of the present invention that was prepared according to Formulation Example 5 was diluted with water so that the active ingredient concentration was set to 500 ppm to prepare a testing agent solution.

Rice seedling (on the developmental stage of the second true leaf) was planted in a polyethylene cup, and the above-mentioned test solutions 5 mL were irrigated into the plant foot, and the plants were held at 25° C. in a greenhouse for 7 days. Twenty (20) heads of three to four instar larvae of rice planthopper (*Nilaparvata lugens*) were released and the plants were held in a greenhouse at 25° C. After 6 days, the number of the surviving insects that were parasitic on the leaves of the rice was examined and the controlling value was calculated by the following equation.

Controlling value (%)={1−($Cb$×$Tai$)/($Cai$×$Tb$)}×100 wherein the symbols in the formula represent the following descriptions.

Cb: Number of the insects before treatment in untreated area;

Cai: Number of the surviving parasitic insects at the time of the investigation in untreated area;

Tb: Number of the insects before treatment in treated area;

Tai: Number of the surviving parasitic insects at the time of the investigation in treated area;

As a result, the treatment with the compound of the present invention showed a controlling value of 90% or more.

Test Example 6

A formulation of the compound of the present invention that was prepared according to Formulation Example 5 was diluted with water so that the active ingredient concentration was set to 500 ppm to prepare a testing agent solution.

Cucumber seedling on the developmental stage of the first true leaf) was planted in a plastic cup, and about 30 heads of cotton aphid (*Aphis gossypii*) were released onto the leaves of the cucumber and allowed to stand for 1 day. The above-mentioned test solutions 20 mL were sprayed into the seedling.

At 6 days post the spraying, the number of the surviving insects that were parasitic on the leaves of the cucumber was examined and the controlling value was calculated by the following equation.

Controlling value (%)={1−($Cb$×$Tai$)/($Cai$×$Tb$)}×100 wherein the symbols in the formula represent the following descriptions.

Cb: Number of the insects before treatment in untreated area;

Cai: Number of the surviving parasitic insects at the time of the investigation in untreated area;

Tb: Number of the insects before treatment in treated area;

Tai: Number of the surviving parasitic insects at the time of the investigation in treated area;

As a result, the treatment with the compound of the present invention showed a controlling value of 90% or more.

Test Example 7

A formulation of the compound of the present invention that was prepared according to Formulation Example 5 was diluted with water so that the active ingredient concentration was set to 500 ppm to prepare a testing agent solution.

Soils were washed off from the cucumber seedlings (on the developmental stage of the first true leaf). The root of the cucumber seedlings was soaked in the above-mentioned test solutions 5 mL, and at one day after the treatment, thirty heads of cotton aphid (*Aphis gossypii*) (all stages of life) were inoculated onto the leaves of the cucumber. At 7 days post the inoculation, the number of the surviving insets that were parasitic on the leaves of the cucumber was examined, and the controlling value was calculated by the following equation.

Controlling value (%) = $\{1-(Cb \times Tai)/(Cai \times Tb)\} \times 100$ wherein the symbols in the formula represent the following descriptions.

Cb: Number of the insects before treatment in untreated area;

Cai: Number of the surviving parasitic insects at the time of the investigation in untreated area;

Tb: Number of the insects before treatment in treated area;

Tai: Number of the surviving parasitic insects at the time of the investigation in treated area;

As a result, the treatment with the compound of the present invention showed a controlling value of 90% or more.

Test Example 8

A formulation of the compound of the present invention that was prepared according to Formulation Example 5 was diluted with water so that the active ingredient concentration was set to 500 ppm to prepare a testing agent solution.

Forty (40) heads of female adult of two spotted spider mites (*Tetranychus urticae*) were released onto kidney beans (immediately after the development of the primary leaf). Next day, the above-mentioned test solutions were sprayed with a spray gun in the dripping amount of the chemical solution. The plants were placed in a thermostatic breeding room (25° C.), and at 13 days post the treatment, the number of the surviving insects was examined, and the controlling value was calculated by the following equation.

Controlling value (%) = {1−(Number of the surviving female adult insects in treated area)/(Number of the surviving female adult insects in untreated area)×100

As a result, the treatment with the compound of the present invention showed a controlling value of 90% or more.

Test Example 9

A Formulation of the compound of the present invention that was prepared according to Formulation Example 5 was diluted with water so that the active ingredient concentration was set to 500 ppm to prepare a testing agent solution.

The bottom of the polyethylene cup having 5.5 cm diameter was matted with the same size of a filter paper, and 0.7 mL of the above-mentioned testing agent solution was added dropwise to the filter, and 30 mg of sucrose as bait was placed in the cup uniformly. Ten (10) heads of female adult housefly (*Musca domestica*) were released into the polyethylene cup and the cup was covered with the lid. After 24 hours, the life and death of housefly was examined, and the number of died insects was counted and the mortality of insects was calculated by the following equation.

Mortality of insects (%) = (Number of dead insects/Number of tested insects)×100

As a result, the treatment with the compound of the present invention showed a mortality of 100%.

Test Example 10

A Formulation of the compound of the present invention that was prepared according to Formulation Example 5 was diluted with water so that the active ingredient concentration was set to 500 ppm to prepare a testing agent solution.

The above-mentioned testing agent solution 0.7 mL was added to 100 mL of ion-exchange water (the active ingredient concentration of 3.5 ppm). Twenty (20) heads of the final instar larvae of common house mosquito (*Culex pipiens pollens*) was released onto the above-mentioned solution. After 24 hours, the life and death of common house mosquito was examined, and the number of died insects was counted and the mortality of insects was calculated by the following equation.

Mortality of insects (%) = (Number of dead insects)/(Number of tested insects)×100

As a result, the treatment with the compound of the present invention showed a mortality of 90% or more.

Test Example 11

Ten (10) mg of the compound of the present invention was dissolved into 3 mL of acetone. Further the agent solution was diluted with acetone to twenty times to prepare the testing agent solution (the active ingredient concentration 167 ppm). African malaria mosquito (*Anopheles gambiae*) adults were subjected to an anesthetic treatment with carbon dioxide gas, and then each of 0.3 μL of the above-mentioned testing agent solution was topically applied to a pronotum of a female insect. A test was carried out 10 heads per group, and after the topical application, the insects were transferred to a cup, and fed with 5% sugar solution. At two days post the topical application, the life and death of African malaria mosquito was examined, and the mortality of insects was calculated by the following equation.

Mortality of insects (%) = (Number of dead insects)/(Number of tested insects)×100

As a result, the treatment with the compound of the present invention showed a mortality of 90% or more.

INDUSTRIAL APPLICABILITY

The compound of the present invention has an efficacy for controlling pests, and thus is useful as an active ingredient for a pest control agent.

The invention claimed is:

1. A pyrimidine compound represented by formula (1):

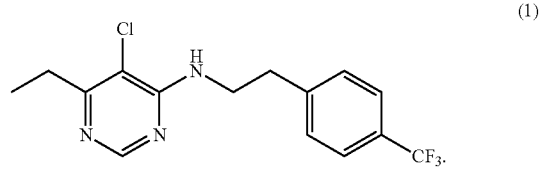 [SMILES: CCc1ncnc(NCCc2ccc(C(F)(F)F)cc2)c1Cl]

2. An agent for controlling pests comprising the pyrimidine compound of claim 1 and an inert active carrier.

3. A method for controlling pests comprising a process of applying an effective amount of the pyrimidine compound of claim 1 to a pest or a habitat where the pest lives.

* * * * *